(12) United States Patent
Schindlbeck et al.

(10) Patent No.: US 10,646,792 B2
(45) Date of Patent: May 12, 2020

(54) PROCESSES FOR SEPARATING AN MTO EFFLUENT

(71) Applicant: UOP LLC, Des Plaines, IL (US)

(72) Inventors: Christopher Schindlbeck, Arlington Heights, IL (US); John J. Senetar, Naperville, IL (US); Joseph A. Montalbano, Elmhurst, IL (US)

(*) Notice: Subject to any disclaimer, the term of this patent is extended or adjusted under 35 U.S.C. 154(b) by 0 days.

(21) Appl. No.: 16/100,570

(22) Filed: Aug. 10, 2018

(65) Prior Publication Data
US 2020/0047079 A1 Feb. 13, 2020

(51) Int. Cl.
| | | |
|---|---|---|
| *B01D 3/14* | (2006.01) |
| *C07C 1/22* | (2006.01) |
| *B01D 3/32* | (2006.01) |
| *B01D 5/00* | (2006.01) |
| *C07C 11/04* | (2006.01) |
| *C07C 11/06* | (2006.01) |
| *C07C 11/08* | (2006.01) |
| *C07C 7/04* | (2006.01) |
| *C07C 1/24* | (2006.01) |
| *C07C 2/86* | (2006.01) |

(52) U.S. Cl.
CPC .......... *B01D 3/143* (2013.01); *B01D 3/322* (2013.01); *B01D 5/0039* (2013.01); *C07C 1/22* (2013.01); *C07C 7/04* (2013.01); *C07C 11/04* (2013.01); *C07C 11/06* (2013.01); *C07C 11/08* (2013.01); *B01D 2256/24* (2013.01); *B01D 2257/70* (2013.01); *C07C 1/24* (2013.01); *C07C 2/86* (2013.01); *C07C 2/862* (2013.01)

(58) Field of Classification Search
None
See application file for complete search history.

(56) References Cited

U.S. PATENT DOCUMENTS

| | | | |
|---|---|---|---|
| 6,166,282 A | 12/2000 | Miller | |
| 7,309,679 B2 | 12/2007 | Karch et al. | |
| 7,423,191 B2 | 9/2008 | Senetar et al. | |
| 9,452,957 B2 | 9/2016 | Senetar et al. | |
| 9,643,897 B2 | 5/2017 | Jan | |
| 2013/0178683 A1 | 7/2013 | Avaullee et al. | |
| 2015/0368168 A1* | 12/2015 | Senetar | C07C 7/005 585/809 |

FOREIGN PATENT DOCUMENTS

| | | |
|---|---|---|
| EP | 1562881 A2 | 1/2012 |
| EP | 2 516 364 | 10/2012 |
| WO | 20040040039 A2 | 5/2004 |
| WO | 2011076751 A1 | 6/2011 |

* cited by examiner

*Primary Examiner* — Ali Z Fadhel

(57) ABSTRACT

A process is presented for removing the fouling problems associated with the product recovery in a methanol to olefins conversion process. The process includes passing the quenched MTO process stream to a product separator, wherein an intermediate stream is generated and includes water and heavier hydrocarbons. The intermediate stream is processed to remove the buildup of heavier hydrocarbons.

20 Claims, 2 Drawing Sheets

PROCESSES FOR SEPARATING AN MTO EFFLUENT

FIELD OF THE INVENTION

Figure 1:
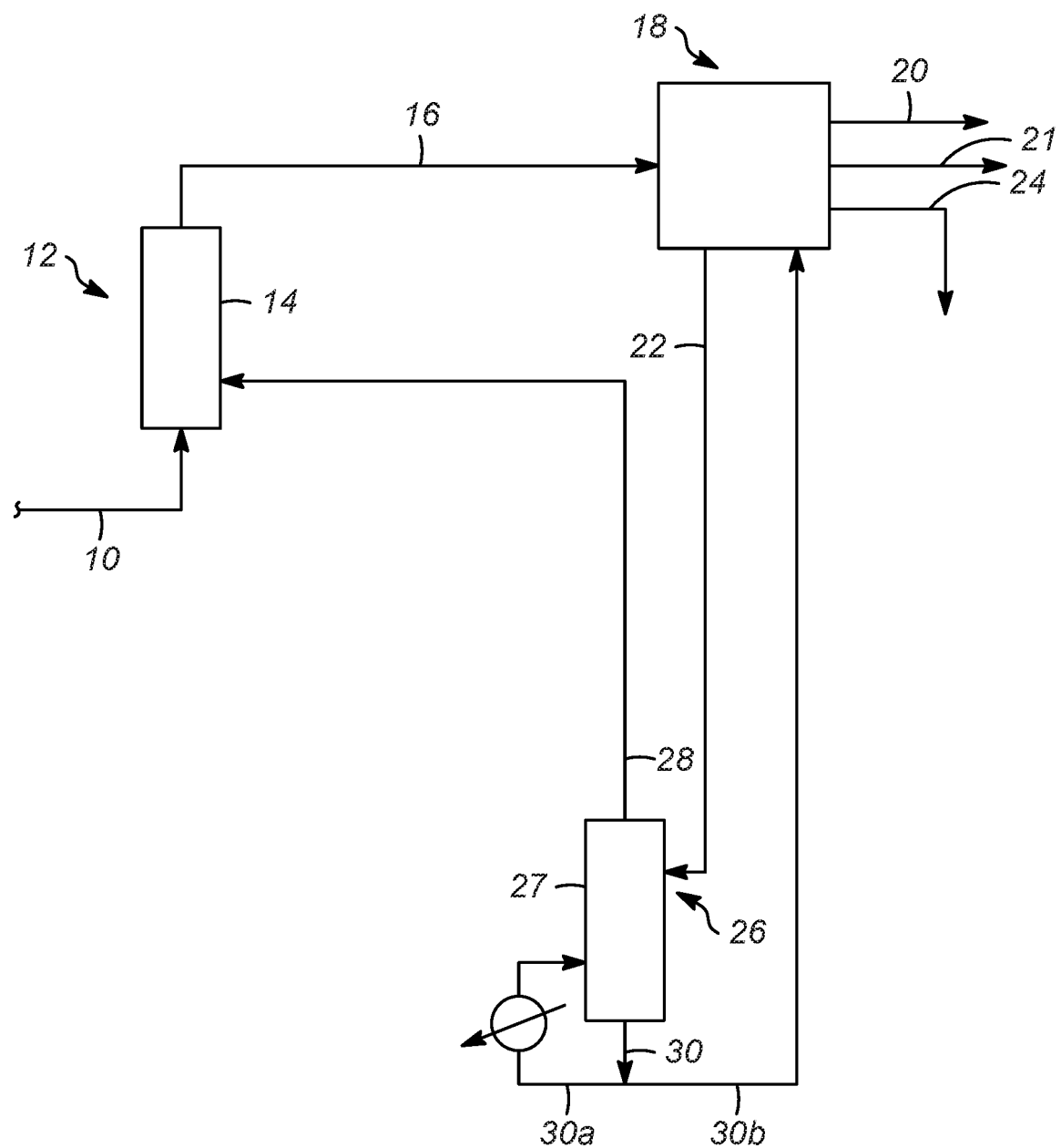

The field of the invention relates to the process of converting oxygenates to olefins. In particular, the invention relates to the recovery of an olefin stream from the effluent from a methanol to olefins reactor, and specifically, to processes which more effectively and efficiently separate and recover heavy hydrocarbons from the effluent of the methanol to olefins reactor.

BACKGROUND OF THE INVENTION

The use of plastics and rubbers are widespread in today's world. The production of these plastics and rubbers are from the polymerization of monomers which are generally produced from petroleum. The monomers are generated by the breakdown of larger molecules to smaller molecules which can be modified. The monomers are then reacted to generate larger molecules comprising chains of the monomers. An important example of these monomers is light olefins, including ethylene and propylene, which represent a large portion of the worldwide demand in the petrochemical industry. Light olefins, and other monomers, are used in the production of numerous chemical products via polymerization, oligomerization, alkylation and other well-known chemical reactions. These monomers are essential building blocks for the modern petrochemical and chemical industries.

Light olefins can be generated through the conversion of oxygenates to olefins. A common process is the methanol to olefins (MTO) conversion process. The process involves many steps and includes recycling of streams such as water generated by the MTO process. However, the MTO conversion process generates solid materials and heavy hydrocarbons that can present fouling issues in the process units. Specifically, in the MTO process, unacceptable levels of contaminants, or heavy components, if not removed, can be carried over to the oxygenate stripper. The subsequent fouling of heat exchangers and downstream devices increased costs, through subsequent energy losses, and need for increased downtime to refurbish fouled devices, in particular heat exchangers. The fouling issues have been found to be the buildup of heavy hydrocarbons including highly substituted aromatics, such as hexamethyl benzene (HMB) and pentamethyl benzene (PMB).

U.S. Pat. No. 9,452,957, the entirety of which is incorporated herein by reference, discloses a process which separates heavy hydrocarbons in an MTO conversion process. While presumably effective for its intended purpose, there is a continual desire for efficient and effective processes for separating heavy hydrocarbons from an MTO reactor effluent.

SUMMARY OF THE INVENTION

One or more processes for separating heavy hydrocarbons from an MTO reactor effluent have been invented. As mentioned above, an MTO reaction zone typically generate ppm levels of heavy hydrocarbons materials or heavy oil. This heavy hydrocarbon material is typically aromatic in nature with an aromatic ring with methyl, ethyl, propyl, and butyl substations on the aromatic rings. While this material is formed in ppm levels some of the heavy oil is trapped in water circulation loops of the product separation zone, increasing the concentration of the heavy hydrocarbons over time.

According to the processes of the present invention, the water recycle loop that allows the heavy oil material to concentrate up is broken up, causing a larger separate oil phase to form in the separation processes. As compressors in the compression zone compress the vapor portions of the MTO effluent, some water, oxygenates, and heavier hydrocarbons are knocked out into a separate liquid phase. It is believed that the heavier hydrocarbon fractions of the liquid knocked after each stage of compression will increase due to the increased solubility caused by the higher oxygenate concentration. In some current processes, this liquid with dissolved heavy oil is sent back to the first stage suction drum where the pressure is lower. The liquid then flashes at the lower pressure and the heavies that were soluble with the higher oxygenate concentration are no longer soluble and form a separate phase. This is avoided in the present processes, thus reducing the amount of free oil that forms in the compressor suction drums and therefore leading to less oil skimming. Since there is less oil in a separate phase, it is likely that the performance of the oxygenate stripper/absorber sections could be improved as well since there is less heavy oil present in a separate phase in the sections. This is believed to improve the operability of the unit.

Therefore, the present invention may be characterized, in at least one aspect, as providing a process for separating heavy hydrocarbons from an MTO reactor effluent by: separating an effluent from an MTO reaction zone in a product separation zone into a vapor stream comprising olefinic hydrocarbons, oxygenates, and steam, and a first liquid stream comprising two phases, a first phase comprising water and a second phase comprising heavy hydrocarbons; compressing the vapor stream in a compression zone having a plurality of stages of compression and being configured to provide at least one compressed liquid stream and a compressed vapor stream, each compressed liquid stream comprising two phases, a first phase comprising water and a second phase comprising heavy hydrocarbons; and, separating the first liquid stream from the product separation zone and the at least one compressed liquid stream from the compression zone in a separation vessel into a hydrocarbon liquid stream and a lean hydrocarbon water stream.

It is contemplated that the separation vessel comprises a settling vessel.

It is also contemplated that the process further includes stripping DME from the compressed vapor stream in a DME stripping zone, wherein the DME stripping zone includes a charge drum and a stripping column, and wherein the compressed vapor stream is provided by the charge drum. The charge drum may provide the compressed liquid stream and, the process by include separating the compressed liquid stream from the charge drum in the separation vessel into the hydrocarbon liquid stream and the lean hydrocarbon water stream.

It is further contemplated that the process includes recovering oxygenates from the lean hydrocarbon water stream in a water wash zone, the water wash zone providing a liquid hydrocarbon stream comprising heavy olefins and a water stream including oxygenates. The water stream from the water wash zone may include DME from the at least one compressed liquid stream.

It is even further contemplated that the compression zone comprises three stages of compression. The first stage of compression may provide a first compressed liquid stream. The second stage of compression may provide a compressed liquid stream.

In another aspect, the present invention may be broadly characterized as providing a process for separating heavy hydrocarbons from an MTO reactor effluent by: passing an effluent from an MTO reaction zone to a product separation zone configured to separate the effluent into a vapor stream and a liquid stream, the effluent comprising light olefins, heavy olefins, water, hydrocarbons, and oxygenates; passing the liquid stream to a separation vessel; passing the vapor stream to a compression zone configured to compress the vapor stream and provide at least two aqueous streams and a compressed vapor stream, wherein the compression zone comprises a plurality of stages of compression; passing the at least two aqueous streams to the separation vessel; recovering a hydrocarbon liquid stream from the separation vessel; and, passing a lean hydrocarbon water stream from the separation vessel to a water wash zone configured to recover oxygenates from the water stream and provide a liquid hydrocarbon stream comprising heavy olefins and a recycle water stream.

It is contemplated that process also includes passing the compressed vapor stream to a charge drum configured to provide an olefin vapor stream comprising light olefins, an intermediate water stream, and an intermediate hydrocarbon liquid stream comprising butanes and heavier hydrocarbons. The process may include passing the intermediate water stream to the separation vessel. The process may also include passing the intermediate hydrocarbon liquid stream to a DME stripping column configured to provide an overhead stream and a bottoms stream and, passing the overhead stream from the DME stripping column to the charge drum. The process may include passing the bottom stream from the DME stripping column to the water wash zone. The process may also further include passing the olefin vapor stream to an oxygenate absorber configured to absorb oxygenates and provide a product light olefin stream. The oxygenate absorber may receive a portion of the water stream from the separation vessel. The process may include passing a bottoms stream from the oxygenate absorber to an oxygenate stripping zone. The process may still further include passing the recycle water stream from the water wash zone to the oxygenate stripping zone.

It is also contemplated that the process includes sensing at least one parameter of the process and generating a signal or data from the sensing; generating and transmitting a signal; or generating and transmitting data.

It is further contemplated that the compression zone comprises at least three stages of compression. A first aqueous stream from the at least two aqueous streams may be provided by the first stage of compression, and a second aqueous stream from the at least two aqueous streams may be provided by the second stage of compression.

Additional aspects, embodiments, and details of the invention, all of which may be combinable in any manner, are set forth in the following detailed description of the invention.

DETAILED DESCRIPTION OF THE DRAWINGS

Figure 2:
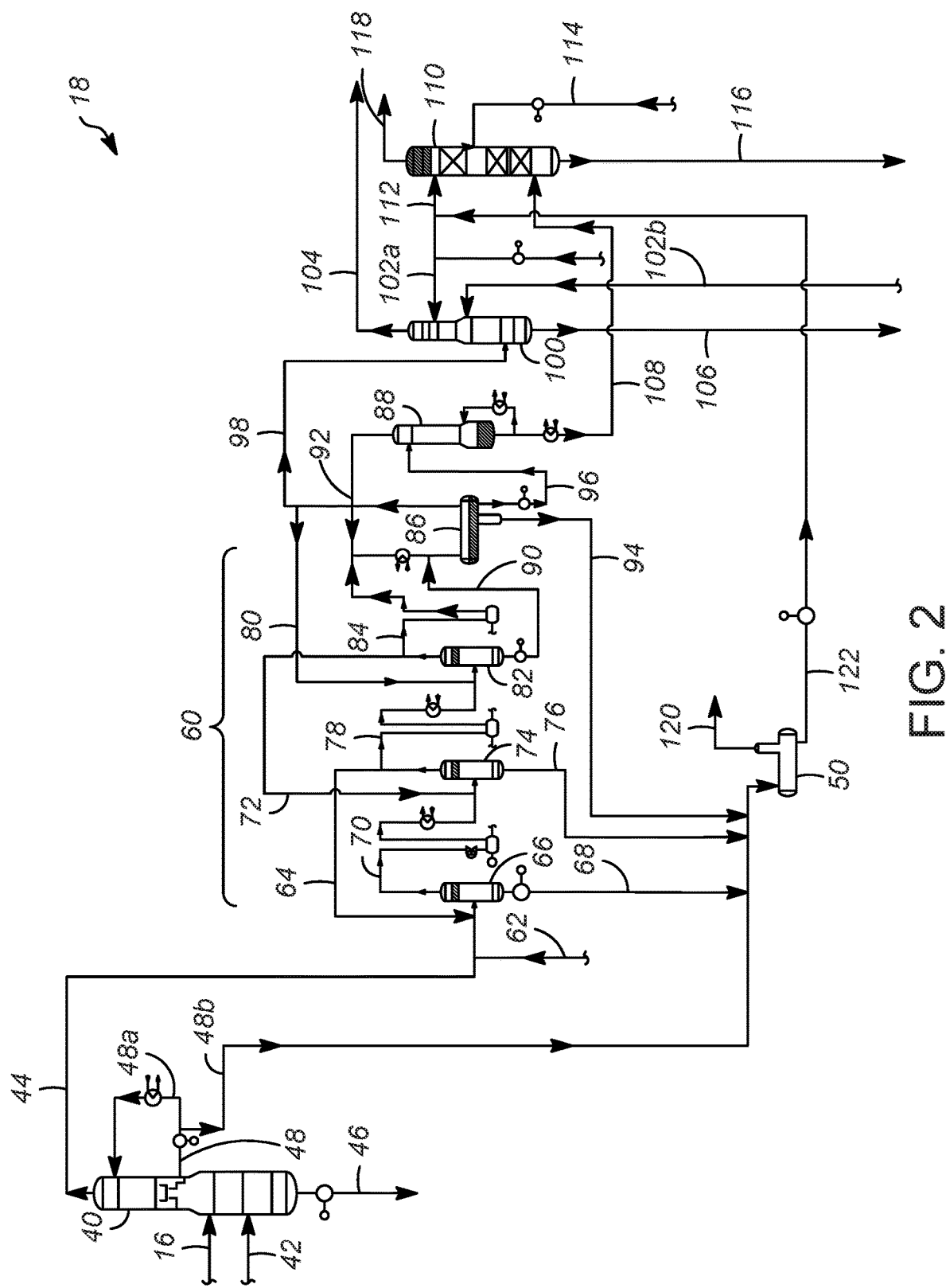

One or more exemplary embodiments of the present invention will be described below in conjunction with the following drawing figures, in which:

FIG. 1 shows a process flow diagram of an exemplary MTO reaction process according to the present invention; and, FIG. 2 shows a process flow diagram for the production separation zone of the MTO reaction of FIG. 1.

DETAILED DESCRIPTION OF THE INVENTION

As mentioned above, processes for separating an MTO effluent have been invented which reduce the buildup of heavy hydrocarbons. According to the present processes, liquid streams comprising mostly water, but including some hydrocarbons, from the multiple suction drums and a charge drum are passed to a settling drum instead of being routed back through the first stage suction drum. The present processes pumps water that contains dissolved oil material and potentially some free oil to the water wash section. The dissolved oil is expected to be easier to separate because it is dissolved in the water.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

As depicted, process flow lines in the figures can be referred to, interchangeably, as, e.g., lines, pipes, branches, distributors, streams, effluents, feeds, products, portions, catalysts, withdrawals, recycles, suctions, discharges, and caustics.

As used herein, the term "rich" can mean an increased amount of a compound or class of compounds in a stream relative to that in another stream.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

With these general principles in mind, one or more embodiments of the present invention will be described with the understanding that the following description is not intended to be limiting.

As shown in FIG. 1, in an MTO conversion processes, an oxygenate feed stream 10 is passed to an MTO reaction zone 12 having at least one reactor 14. The at least one reactor 14 of the MTO reaction zone 12 may be a fluidized bed reactor and includes an MTO catalyst that converts methanol, as well as dimethylether (DME), or both from the oxygenate feed stream 10 into olefins. Such MTO reactors and catalysts are known in the art, for example, in U.S. Pat. Nos. 6,166,282, 7,309,679, 7,423,191, and 9,643,897, the entireties of which are incorporated by reference herein.

An effluent from the effluent an MTO reaction zone 12 includes light olefins, oxygenates, and water. After separating catalyst from the effluent, an effluent stream 16 from the MTO reaction zone 12 may be passed to a product separation zone 18 configured to separate the effluent stream 16 into a product stream 20 comprising light olefins, a heavy hydrocarbon stream 21, and an aqueous stream 22 comprising oxygenates and water. Additionally, the product separation zone 18 may provide a waste water stream 24. The product separation zone 18 is shown in more detail in FIG. 2 and discussed below. The product stream 20, as is known, may be passed to a fractionation section (not shown) configured to separate the product stream 20 into different components streams.

The aqueous stream 22, comprising oxygenates and water, may be passed to an oxygenate stripping zone 26 having an oxygenate stripper 27 configured to provide an oxygenate-rich stream 28 and a water stream 30 with reduced amount of oxygenates. A first portion 30a of the water stream 30 may be heated and routed to the oxygenate stripper 27. A second portion 30b of the water stream 30 may be passed back to the product separation zone 18. Typically, the oxygenate-rich stream 28, or a portion thereof, is recycled to the MTO reaction zone 12 to allow the methanol and DME therein to react.

Turning to FIG. 2, the product separation zone 18 includes a product separator 40 which receives the effluent stream 16, as well as a water stream 42, and generates a first vapor stream 44 comprising olefinic hydrocarbons, oxygenates, and steam, a bottoms stream 46 comprising waste water, and a first liquid stream 48 comprising two liquid phases, the first being mostly water and the second being mostly heavy hydrocarbons. A portion 48a of the first liquid stream 48 is cooled and pumped back to the product separator 40, while a second portion 48b of the first liquid stream 48 is passed to a separation vessel 50, discussed in more detail below. The first vapor stream 44 is passed to a compression zone 60.

The compression zone 60 includes a plurality of stages of compression, preferably, at least two stages, and most preferably three stages of compression. As shown in the exemplary embodiment of FIG. 2, the first vapor stream 44, after being mixed with a stream of water 62 and a vapor recycle stream 64, is passed to a first knockout drum 66. A liquid bottoms stream 68 comprising mostly water is passed to the separation vessel 50. A vapor overhead stream 70 from the first knockout drum 66 is compressed, cooled, combined with a second vapor recycle stream 72 and passed to a second knockout drum 74.

A second liquid bottoms stream 76, being a compressed liquid stream and comprising mostly water, as well as some heavy hydrocarbons, is passed to the separation vessel 50. A second vapor overhead stream 78 from the second knockout drum 74 is compressed, cooled, combined with a third vapor recycle stream 80 and passed to a third knockout drum 82. A portion of the second vapor overhead stream 78 from the second knockout drum 74 is used as a vapor recycle stream 64 that is used for compressor surge protection.

A third vapor overhead stream 84, comprising a compressed vapor stream, from the third knockout drum 82 is compressed and cooled and then passed to a charge drum 86 for a DME stripper 88. A portion of the third vapor overhead stream 84 from the third knockout drum 82 is used as the second vapor recycle stream 72, again used for surge protection. Prior to being passed into the charge drum 86, the third vapor overhead stream 84 is combined with a third liquid bottom stream 90 and a DME stripper overhead vapor 92 (discussed below).

The charge drum 86 provides a compressed liquid stream 94 comprising mostly water, but also some heavy hydrocarbons. A portion of a compressed vapor stream 98 is the third vapor recycle stream 80, used for compressor surge control. The remainder of the compressed vapor stream 98 is passed to an oxygenate absorber 100.

The oxygenate absorber 100 also receives water streams 102a, 102b and removes residual oxygenates to recycle the recovered oxygenates to the oxygenate stripper 27 (see, FIG. 1) as stream 106. The oxygenate absorber 100 generates an oxygenate overhead stream 104 being a product light olefin stream that comprises the light olefins produced in the MTO reactor 14, and an oxygenate bottoms stream 106 comprising water and oxygenates. The further processing of the oxygenate overhead stream 104 is known in the art and may include a caustic scrubber and a drier to recover the olefins generated by the MTO reaction.

Returning to the charge drum 86, the liquid hydrocarbon stream 96 is passed to the DME stripper 88 to recover olefins in the DME stripper overhead stream 92. A DME stripper bottoms stream 108, comprising C4+olefins and oxygenates including DME, may be cooled and passed to a water wash column 110. The water wash column 110, which receives a water stream 112 and a methanol containing stream 114 removes oxygenates from the DME stripper bottoms stream 108 enabling the oxygenates to be recycled to the oxygenate stripper 27 (see, FIG. 1) as, for example, stream 22 in a water stream 116. A liquid hydrocarbon stream 118 comprising heavy olefins from the water wash column 110 can be passed to downstream processing units. One such processing unit is an olefin cracking process unit to crack heavier olefins and to further increase the yields of light olefins from the MTO process.

Once again, returning to the charge drum 86, the compressed liquid stream 94 is passed to the separation vessel 50. In known processes, only the second portion 48b of the first liquid stream 48 and the liquid bottoms stream 68 from the first knock out drum 66 are passed to the separation vessel 50. This leads to the undesired buildup of heavy hydrocarbons in the water recirculation used in the MTO processes. Accordingly, as mentioned above, the second liquid bottoms stream 76 (being a compressed liquid stream) and the compressed liquid stream 94 from the second and third stages of compression are also passed to the separation vessel 50—resulting in the reduction of heavy hydrocarbons build up. The second liquid bottoms stream 76 and the compressed liquid stream 94 have two phases, two phases, a first phase comprising water and a second phase comprising heavy hydrocarbons. Additionally, the heavy hydrocarbons are maintained in liquid phase-either as dissolved oil in the water, or as a separate phase. This oil is believed to be easier to separate in liquid phase.

Thus, the separation vessel 50 may be a settling unit which generates an upper phase comprising hydrocarbons and a lower aqueous phase. The separation vessel 50 may include a coalescer for agglomerating small hydrocarbon droplets, or other means known for separating a mixture of hydrocarbons and water. The upper phase may be drawn off as a second liquid hydrocarbon stream 120, which may or may not be passed to the wash column 110. The lower phase in the separation vessel 50 may be withdrawn as a lean hydrocarbon water stream 122 and passed to the oxygenate absorber 100 as the water stream 102a, the water wash column 110 as water stream 112, or both.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein. For example, one or more lines could include a sensor indicating an amount of heavy hydrocarbons in a stream. If the amount of heavy hydrocarbons is at or below an acceptable level, the processes could control the compression stages to achieve a desired compression level.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

SPECIFIC EMBODIMENTS

While the following is described in conjunction with specific embodiments, it will be understood that this description is intended to illustrate and not limit the scope of the preceding description and the appended claims.

A first embodiment of the invention is a process for separating heavy hydrocarbons from an MTO reactor effluent, the process comprising separating an effluent from an MTO reaction zone in a product separation zone into a vapor stream comprising olefinic hydrocarbons, oxygenates, and steam, and a first liquid stream comprising two phases, a first phase comprising water and a second phase comprising heavy hydrocarbons; compressing the vapor stream in a compression zone having a plurality of stages of compression and being configured to provide at least one compressed liquid stream and a compressed vapor stream, each compressed liquid stream comprising two phases, a first phase comprising water and a second phase comprising heavy hydrocarbons; and, separating the first liquid stream from the product separation zone and the at least one compressed liquid stream from the compression zone in a separation vessel into a hydrocarbon liquid stream and a lean hydrocarbon water stream. An embodiment of the invention is one, any or all of prior embodiments in this paragraph up through the first embodiment in this paragraph wherein the separation vessel comprises a settling vessel. An embodiment of the invention is one, any or all of prior embodiments in this paragraph up through the first embodiment in this paragraph further comprising stripping DME from the compressed vapor stream in a DME stripping zone, wherein the DME stripping zone includes a charge drum and a stripping column, and wherein the compressed vapor stream is provided by the charge drum. An embodiment of the invention is one, any or all of prior embodiments in this paragraph up through the first embodiment in this paragraph, wherein the charge drum provides the compressed liquid stream, and further comprising separating the compressed liquid stream from the charge drum in the separation vessel into the hydrocarbon liquid stream and the lean hydrocarbon water stream. An embodiment of the invention is one, any or all of prior embodiments in this paragraph up through the first embodiment in this paragraph further comprising recovering oxygenates from the lean hydrocarbon water stream in a water wash zone, the water wash zone providing a liquid hydrocarbon stream comprising heavy olefins and a water stream including oxygenates. An embodiment of the invention is one, any or all of prior embodiments in this paragraph up through the first embodiment in this paragraph wherein the water stream from the water wash zone includes DME from the at least one compressed liquid stream. An embodiment of the invention is one, any or all of prior embodiments in this paragraph up through the first embodiment in this paragraph wherein the compression zone comprises three stages of compression. An embodiment of the invention is one, any or all of prior embodiments in this paragraph up through the first embodiment in this paragraph, wherein a first stage of compression provides a first compressed liquid stream. An embodiment of the invention is one, any or all of prior embodiments in this paragraph up through the first embodiment in this paragraph, wherein a second stage of compression provides a second compressed liquid stream.

A second embodiment of the invention is a process for separating heavy hydrocarbons from an MTO reactor effluent, the process comprising passing an effluent from an MTO reaction zone to a product separation zone configured to separate the effluent into a vapor stream and a liquid stream, the effluent comprising light olefins, heavy olefins, water, hydrocarbons, and oxygenates; passing the liquid stream to a separation vessel; passing the vapor stream to a compression zone configured to compress the vapor stream and provide at least two aqueous streams and a compressed vapor stream, wherein the compression zone comprises a plurality of stages of compression; passing the at least two aqueous streams to the separation vessel; recovering a hydrocarbon liquid stream from the separation vessel; and, passing a lean hydrocarbon water stream from the separation vessel to a water wash zone configured to recover oxygenates from the water stream and provide a liquid hydrocarbon stream comprising heavy olefins and a recycle water stream. An embodiment of the invention is one, any or all of prior embodiments in this paragraph up through the second embodiment in this paragraph further comprising passing the compressed vapor stream to a charge drum configured to provide an olefin vapor stream comprising light olefins, an intermediate water stream, and an intermediate hydrocarbon liquid stream comprising butanes and heavier hydrocarbons. An embodiment of the invention is one, any or all of prior embodiments in this paragraph up through the second embodiment in this paragraph further comprising passing the intermediate water stream to the separation vessel. An embodiment of the invention is one, any or all of prior embodiments in this paragraph up through the second embodiment in this paragraph further comprising passing the intermediate hydrocarbon liquid stream to a DME stripping column configured to provide an overhead stream and a bottoms stream; and, passing the overhead stream from the DME stripping column to the charge drum. An embodiment of the invention is one, any or all of prior embodiments in this paragraph up through the second embodiment in this paragraph further comprising passing the bottom stream from the DME stripping column to the water wash zone. An embodiment of the invention is one, any or all of prior embodiments in this paragraph up through the second embodiment in this paragraph further comprising passing the olefin vapor stream to an oxygenate absorber configured to absorb oxygenates and provide a product light olefin stream. An embodiment of the invention is one, any or all of prior embodiments in this paragraph up through the second embodiment in this paragraph wherein the oxygenate absorber receives a portion of the water stream from the separation vessel. An embodiment of the invention is one, any or all of prior embodiments in this paragraph up through the second embodiment in this paragraph further comprising passing a bottoms stream from the oxygenate absorber to an oxygenate stripping zone. An embodiment of the invention is one, any or all of prior embodiments in this paragraph up through the second embodiment in this paragraph further comprising passing the recycle water stream from the water wash zone to the oxygenate stripping zone. An embodiment of the invention is one, any or all of prior embodiments in this paragraph up through the second embodiment in this paragraph further comprising at least one of sensing at least one parameter of the process and generating a signal or data from the sensing; generating and transmitting a signal; or generating and transmitting data. An embodiment of the invention is one, any or all of prior embodiments in this paragraph up through the second embodiment in this paragraph wherein the compression zone comprises at least three stages of compression, and wherein a first aqueous stream from the at least two aqueous streams is provided by the first stage of compression, and wherein a second aqueous stream from the at least two aqueous streams is provided by the second stage of compression.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for separating heavy hydrocarbons from an MTO reactor effluent, the process comprising:
   separating an effluent from an MTO reaction zone in a product separation zone into a vapor stream comprising olefinic hydrocarbons, oxygenates, and steam, and a first liquid stream comprising two phases, a first phase comprising water and a second phase comprising heavy hydrocarbons;
   compressing the vapor stream in a compression zone having a plurality of stages of compression and being configured to provide at least one compressed liquid stream and a compressed vapor stream, each compressed liquid stream comprising two phases, a first phase comprising water and a second phase comprising heavy hydrocarbons; and,
   separating the first liquid stream from the product separation zone and the at least one compressed liquid stream from the compression zone in a separation vessel into a hydrocarbon liquid stream and a lean hydrocarbon water stream.

2. The process of claim 1 wherein the separation vessel comprises a settling vessel.

3. The process of claim 1 further comprising:
   stripping DME from the vapor stream in a DME stripping zone, wherein the DME stripping zone includes a charge drum and a stripping column, and wherein the compressed vapor stream is provided by the charge drum.

4. The process of claim 3, wherein the charge drum provides the at least one compressed liquid stream, and further comprising:
   separating the at least one compressed liquid stream from the charge drum in the separation vessel into the hydrocarbon liquid stream and the lean hydrocarbon water stream.

5. The process of claim 1 further comprising:
   recovering oxygenates from the lean hydrocarbon water stream in a water wash zone, the water wash zone providing a liquid hydrocarbon stream comprising heavy olefins and a water stream including oxygenates.

6. The process of claim 5 wherein the water stream from the water wash zone includes DME from the at least one compressed liquid stream.

7. The process of claim 1 wherein the compression zone comprises three stages of compression.

8. The process of claim 7, wherein a first stage of compression provides a first compressed liquid stream.

9. The process of claim 8, wherein a second stage of compression provides a second compressed liquid stream.

10. A process for separating heavy hydrocarbons from an MTO reactor effluent, the process comprising:
    passing an effluent from an MTO reaction zone to a product separation zone configured to separate the effluent into a vapor stream comprising olefinic hydrocarbons, oxygenates, and steam and a liquid stream;
    passing the liquid stream to a separation vessel;
    passing the vapor stream to a compression zone configured to compress the vapor stream and provide at least two aqueous streams and a compressed vapor stream, each aqueous stream comprising two phases, a first phase comprising water and a second phase comprising heavy hydrocarbons, wherein the compression zone comprises a plurality of stages of compression;

passing the at least two aqueous streams to the separation vessel;

recovering a hydrocarbon liquid stream from the separation vessel; and, passing a lean hydrocarbon water stream from the separation vessel to a water wash zone configured to recover oxygenates from the water stream and provide a liquid hydrocarbon stream comprising heavy olefins and a recycle water stream.

11. The process of claim 10 further comprising:

passing the compressed vapor stream to a charge drum configured to provide an olefin vapor stream comprising light olefins, an intermediate water stream, and an intermediate hydrocarbon liquid stream comprising butanes and heavier hydrocarbons.

12. The process of claim 11 further comprising:

passing the intermediate water stream to the separation vessel.

13. The process of claim 11 further comprising:

passing the intermediate hydrocarbon liquid stream to a DME stripping column configured to provide an overhead stream and a bottoms stream; and, passing the overhead stream from the DME stripping column to the charge drum.

14. The process of claim 13 further comprising:

passing the bottom stream from the DME stripping column to the water wash zone.

15. The process of claim 11 further comprising:

passing the olefin vapor stream to an oxygenate absorber configured to absorb oxygenates and provide a product light olefin stream.

16. The process of claim 15 wherein the oxygenate absorber receives a portion of the water stream from the separation vessel.

17. The process of claim 16 further comprising:

passing a bottoms stream from the oxygenate absorber to an oxygenate stripping zone.

18. The process of claim 17 further comprising:

passing the recycle water stream from the water wash zone to the oxygenate stripping zone.

19. The process of claim 10 further comprising at least one of:

sensing at least one parameter of the process and generating a signal or data from the sensing;

generating and transmitting a signal; or generating and transmitting data.

20. The process of claim 10 wherein the compression zone comprises at least three stages of compression, and wherein a first aqueous stream from the at least two aqueous streams is provided by the first stage of compression, and wherein a second aqueous stream from the at least two aqueous streams is provided by the second stage of compression.

* * * * *